United States Patent [19]

Tuneberg et al.

[11] Patent Number: 5,722,826
[45] Date of Patent: Mar. 3, 1998

[54] BONDING PAD

[75] Inventors: Lee H. Tuneberg; William P. Gagin, both of Sheboygan, Wis.

[73] Assignee: American Orthodontics Corporation, Sheboygan, Wis.

[21] Appl. No.: 803,015

[22] Filed: Feb. 21, 1997

Related U.S. Application Data

[60] Provisional application No. 60/012,005, Feb. 21, 1996.
[51] Int. Cl.[6] ............................................. A61C 7/00
[52] U.S. Cl. ......................................................... 433/9
[58] Field of Search ........................................ 433/8, 9

[56] References Cited

U.S. PATENT DOCUMENTS 4,068,379  1/1978  Miller et al. .
4,243,386  1/1981  Kawaguchi ................................. 433/9
4,889,485  12/1989  Iida ............................................ 433/9
5,295,823  3/1994  Farzin-Nia .................................. 433/9
5,441,409  8/1995  Tuneberg ................................... 433/23
5,480,301  1/1996  Farzin-Nia et al. ....................... 433/9

FOREIGN PATENT DOCUMENTS 3519213  6/1986  Germany .................................... 433/8

*Primary Examiner*—Cary E. O'Connor
*Attorney, Agent, or Firm*—Lloyd L. Zickert

[57] ABSTRACT

A bonding pad for an orthodontic attachment to be bonded to a tooth, including a foil or plate having a photoetched surface, and a layer of mesh material diffusion bonded to the photoetched surface of the foil, thereby greatly increasing the bonding strength of the attachment to which the bonding pad is secured.

30 Claims, 3 Drawing Sheets

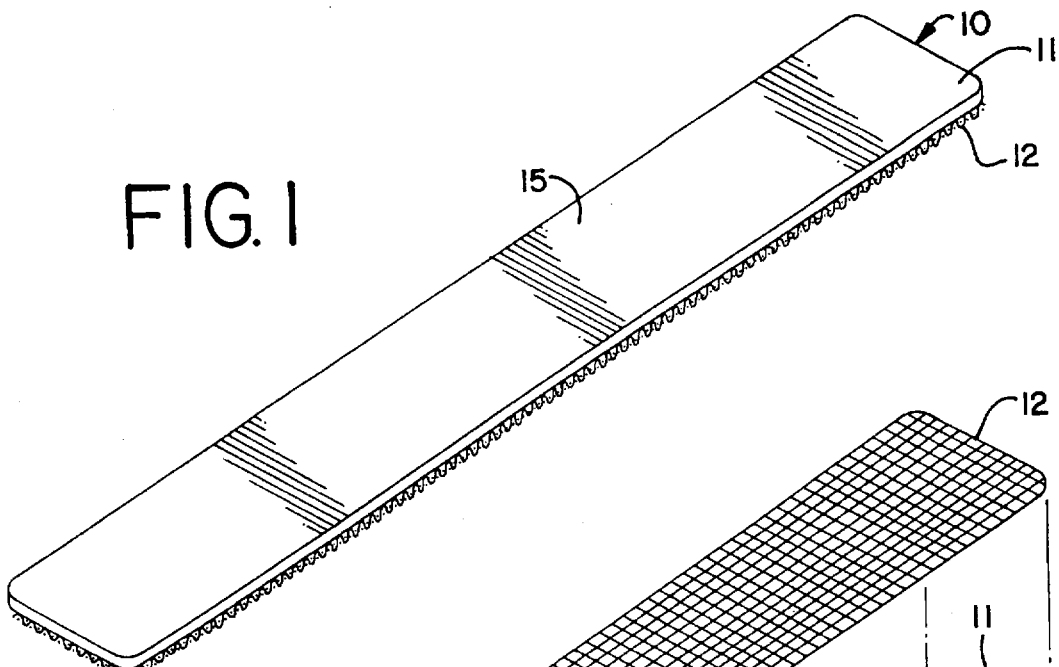
FIG. 1
FIG. 2
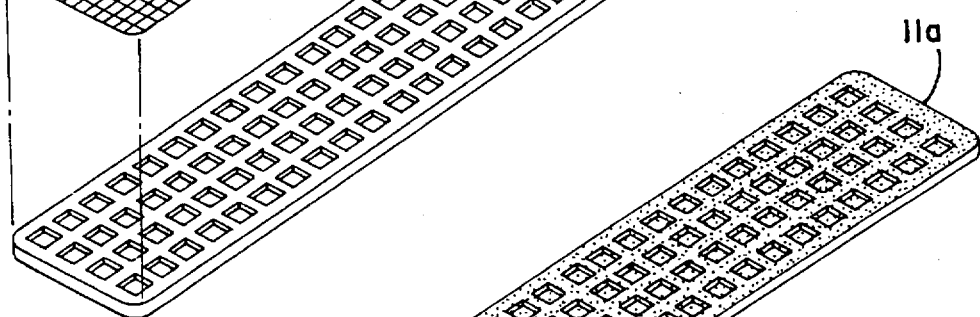
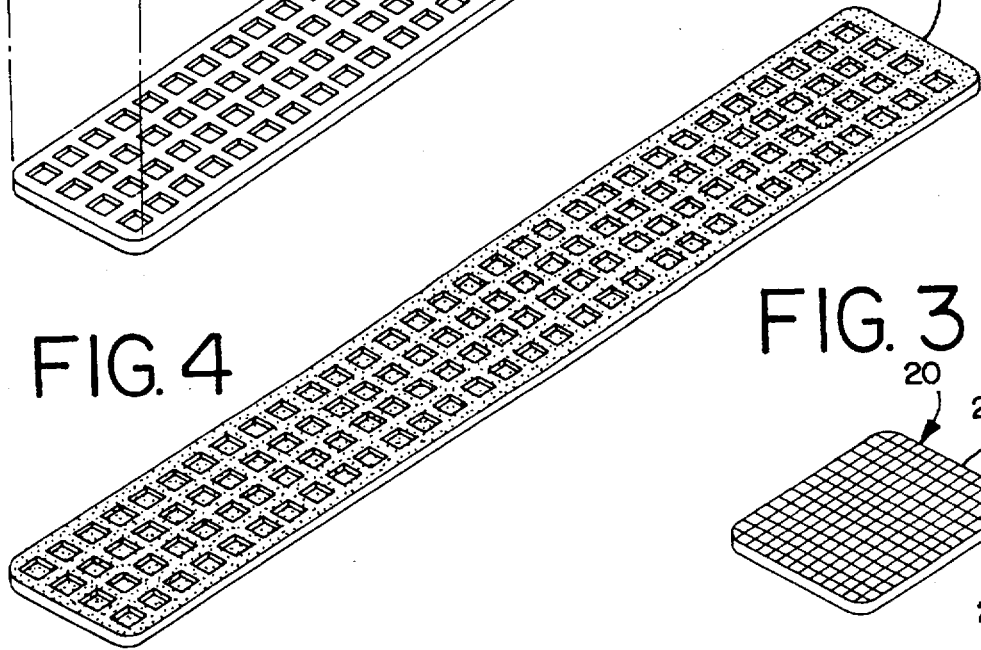
FIG. 4
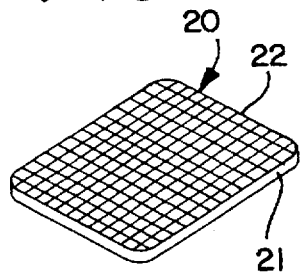
FIG. 3

BONDING PAD

This application claims the benefit of U.S. provisional application Ser. No. 60/012,005 filed Feb. 21, 1996.

This invention relates in general to an improved bonding pad for an orthodontic attachment to increase the bondability of an attachment to the tooth of a person, and more particularly to a bonding pad including a layer of foil having a photoetched surface on one side and having a layer of mesh diffusion bonded to the photoetched surface.

BACKGROUND OF THE INVENTION

With the advent of bonding techniques developed for bonding orthodontic attachments directly to the teeth, it has been desired to have the best possible bond strength between the appliance and the teeth, so that an appliance will remain in bonded position throughout the treatment of a patient with the attachments. Thus, a variety of bonding bases have been developed for orthodontic attachments such as brackets, and the one most commonly used for metal brackets is a mesh/foil bonding pad such as disclosed in U.S. Pat. No. 4,068,379 where a layer of mesh material is secured to a layer of foil to define a bonding pad that may then be suitably secured to an orthodontic bracket or attachment. This patent particularly teaches that the mesh may be secured to the foil by various techniques including sintering or diffusion bonding.

It has also been suggested that a plurality of piggy-backed mesh layers secured to a foil layer will provide a bonding pad having greater bonding strength when bonded to a tooth as disclosed in U.S. Pat. No. 4,889,485.

It has further been known to provide a bonding base having a photoetched surface that has been sandblasted to roughen the surface, as disclosed in U.S. Pat. No. 4,243,386.

It has also been well known to provide photoetched bands to enhance the cementing of a band to a tooth as disclosed in U.S. Pat. No. 5,441,409.

Moreover, it has been known to treat the surface of a bonding base to provide a secondary mechanical bond enhancement by surface roughening with ion bombardment or other etching processes, the flame spray coating of particles onto a surface, and the sandblasting as above mentioned, as disclosed in U.S. Pat. Nos. 5,295,823 and 5,480,301.

While several of the prior art bonding pads have provided a good bonding strength for bonding orthodontic attachments to teeth with a suitable bonding adhesive, there has always been a desire to provide a better bonding pad that would have greater bonding strength, and particularly with a suitable secondary mechanical locking enhancement.

SUMMARY OF THE INVENTION

The bonding pad of the present invention provides both primary and secondary bonding enhancements wherein the pad includes a foil having a photoetched surface and a layer of mesh material suitably secured to the photoetched surface such as by diffusion bonding. The photoetched surface provides a secondary bond interlock, while the mesh provides a primary bond interlock, thereby greatly increasing the strength of the bond between the bonding pad attached to a bracket and a tooth. Further, the present invention also includes a modification wherein the photoetched surface may be suitably treated prior to the securing of the mesh layer to the photoetched surface to thereby further improve the bonding ability of the pad of the present invention. Also, the invention may include a photoetched foil having a sheet or layer of mesh diffusion bonded to the foil to define a laminated product, after which the product is suitably sandblasted or otherwise treated to further roughen or texturize the photoetched surface and the mesh layer. Any suitable method of treating the photoetched surface may be provided, such as sandblasting, flame-spraying of particles, ion bombardment etch, plasma etch, or any other suitable treatment to increase surface area.

Accordingly, it is a principal object of the present invention to provide a new and improved bonding pad or base for bonding orthodontic attachments secured to the pad to the surface of a tooth with a suitable bonding material.

Another object of the present invention is to provide a new and improved bonding pad for orthodontic attachments which includes a foil having a photoetched surface defining a secondary mechanical lock with the bonding material and a layer of mesh material suitably secured to the photoetched surface to provide a primary mechanical lock with the bonding material.

Still another object of the invention is to provide a bonding pad that includes a photoetched foil having a mesh layer diffusion bonded to the foil, and which is thereafter subjected to a sandblasting procedure.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is a perspective view of a strip of stock material prepared to provide bonding pads according to the present invention;

FIG. 2 is an exploded view of the stock material of FIG. 1 showing the foil having the photoetched surface and a layer of mesh material separated from the foil which would ultimately be secured to the foil in a suitable manner;

FIG. 3 is a perspective view of the bonding pad according to the present invention and showing the bonding side of the pad;

FIG. 4 is a modification of the stock material used for making bonding pads according to the present invention in that it shows only the foil which has been photoetched on one surface and where the surface is treated so as to further enhance the bonding strength of the pad;

DESCRIPTION OF THE INVENTION

Figure 5:
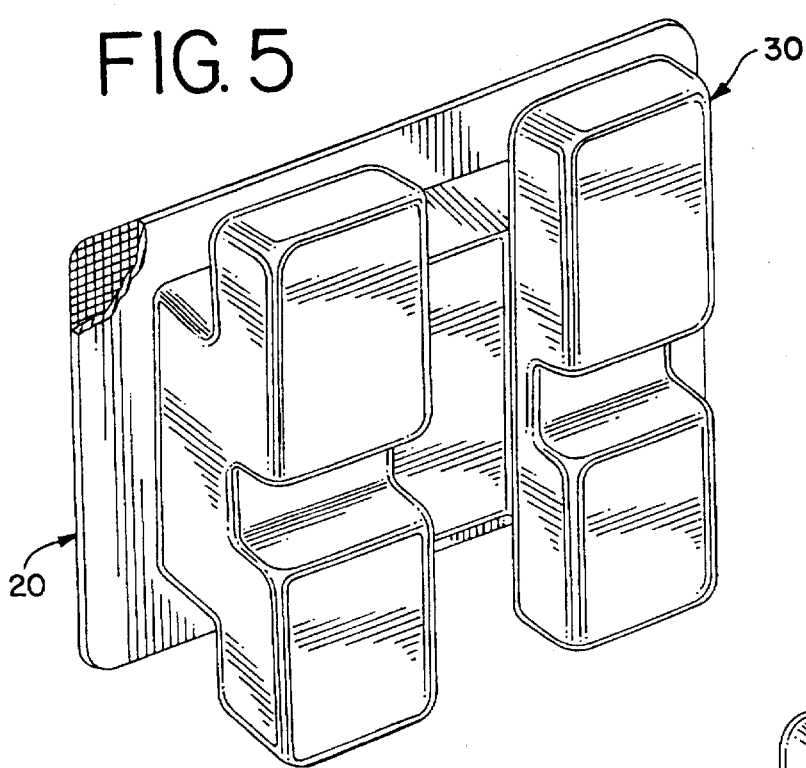
FIG. 5 is a perspective view of an orthodontic bracket having a bonding pad according to the present invention secured thereto.

Referring now to the drawings, and particularly to FIGS. 1 and 2, a strip of bonding pad stock material is shown from which bonding pads of a suitable size may be cut, stamped, or otherwise formed. The stock material is generally indicated by the numeral 10 and includes a layer of foil 11 and a layer of woven mesh 12. Preferably, the foil and the mesh are of a suitable stainless steel, although they could be made of any other suitable metals including titanium. More specifically, the mesh could be made of 316L stainless steel having a mesh count of about 50 to 100 and a wire size of about 0.003 to 0.0075 inches (0.08 to 0.19 mm). Further, the foil may be of any suitable thickness such as about 0.005 to 0.015 inches (0.13 to 0.38 mm).

The foil or plate 11 includes a substantially smooth upper surface 15, as seen in FIG. 1, and a photoetched lower surface 16, as seen in FIG. 2. Thus, the foil 11, when made, will have a suitable photoetched pattern on one surface such as the pattern of square pockets shown in FIG. 2. It will be appreciated that any suitable photoetched pattern may be utilized such as the various photoetched patterns illustrated in the above identified U.S. Pat. No. 5,441,409, which is incorporated herein by reference as to the photoetched patterns.

It shall also be appreciated that the photoetched surface 16 may optionally be treated to further enhance its bonding capability as illustrated in the embodiment of FIG. 4, by the modified foil 11a. The surface may be treated in any suitable manner in order to additionally roughen the surface and/or upset the metal surface to increase surface area. For example, the surface may be sandblasted, or treated with ion bombardment to provide a roughened surface. Additionally, it should be appreciated that the surface could be flame-sprayed with particles such as shown in U.S. Pat. Nos. 5,295,823 and 5,480,301. Also, the surface may be subjected to chemical etching, bead blasting, plasma spraying, HVOF spray, or plasma etching. Thus, any type of surface roughening treatment may be used prior to bonding the mesh.

Figure 8:
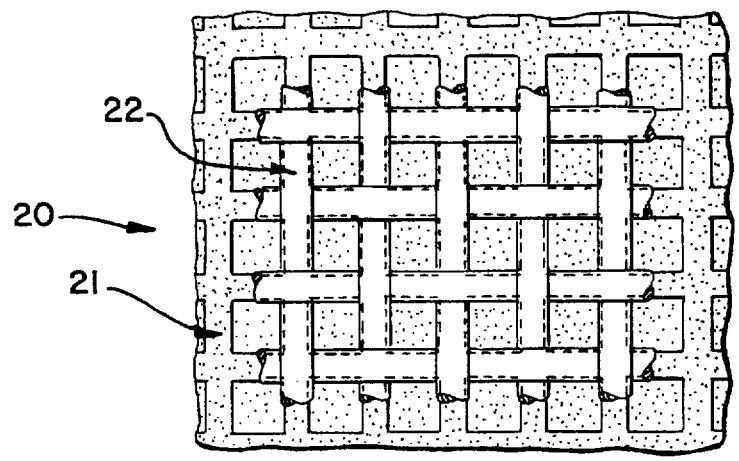
FIG. 8 is a greatly enlarged fragmentary plan view of the attaching side of the bonding pad according to the invention showing the wire mesh overlying the photoetched foil with the mesh oriented at 0° with respect to the foil to show the coaction of the mesh wires with the pockets.
Figure 9:
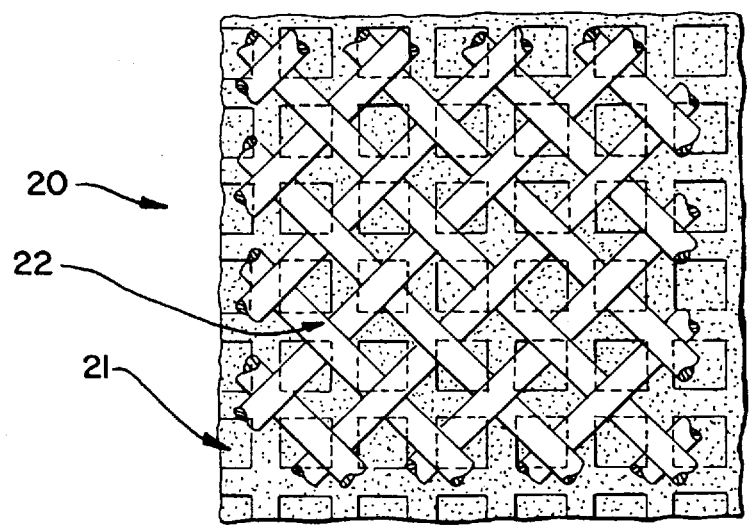
FIG. 9 is a view similar to FIG. 8 but showing the mesh oriented at 45° to the foil.
Figure 10:
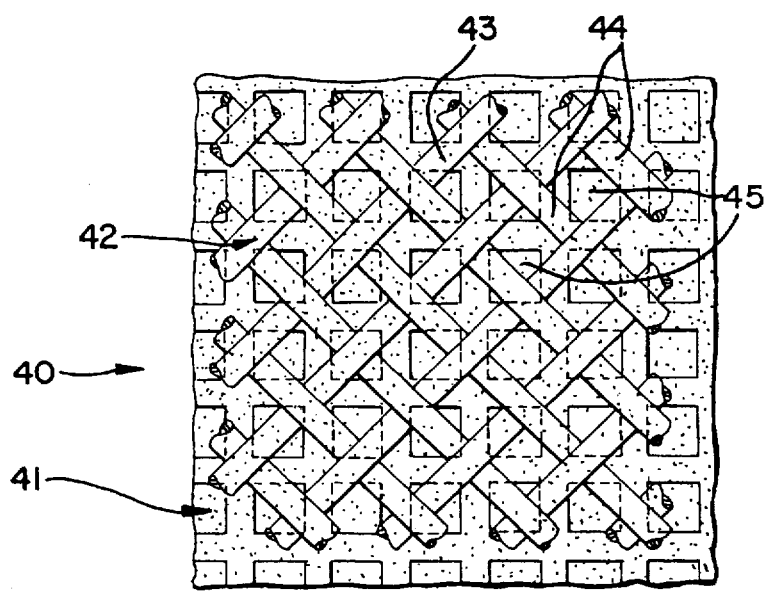
FIG. 10 is a view similar to FIG. 9 but additionally illustrating the bonding side of the pad to be sandblasted.

After the foil 11 has been prepared with its photoetched surface, whether or not the surface is further treated, the layer of mesh 12 is suitably secured to the foil so that it will not delaminate. As above mentioned, the mesh may be diffusion bonded to the photoetched surface of the foil in a manner disclosed in U.S. Pat. No. 4,068,379 to form a foil/mesh laminate. Diffusion bonding would usually include subjecting the mesh/foil composite to a plurality of calendering operations under heat and pressure such as to effectively permanently bond the mesh and foil together. Further, the woven mesh includes warp and woof wires that may be oriented at 0°, 45°, or any suitable angle to the photoetched foil. Mesh diffusion bonded when oriented at 45°, as shown in FIGS. 9 and 10, coacts with the etched pockets to a more significant degree than mesh bonded at 0°, as shown in FIG. 8, because more wires of the mesh cross the etched pockets resulting in creating additional mechanical locking for the bonding adhesive to remain with the pad when the pad and bracket mounted thereon is removed from a tooth under shear force. Although not illustrated in FIG. 7, it will be appreciated that at least some portion of the mesh wires may be forced into the pockets of the textured photoetched surface of the foil by the calendering operations and be bonded to the bottoms of the pockets. However, any suitable method of permanently securing the mesh to the photoetched surface of the foil is acceptable.

Thereafter, the foil/mesh material, as a laminate, is subjected to suitable cutting, punching, stamping or other forming operations in order to produce a bonding pad of a suitable size such as the bonding pad 20 illustrated in FIG. 3. It will then be understood that this bonding pad includes a foil layer 21 that has a photoetched surface and a mesh layer 22 which is bonded to the photoetched surface of the foil 21. Thereafter, it may be desired to add a curvature to the bonding base so that it will better conform and mate to the curved surface of a tooth when applied to a tooth. It is well known to provide curvatures to bonding bases for enhancing the fit on a tooth.

Figure 6:
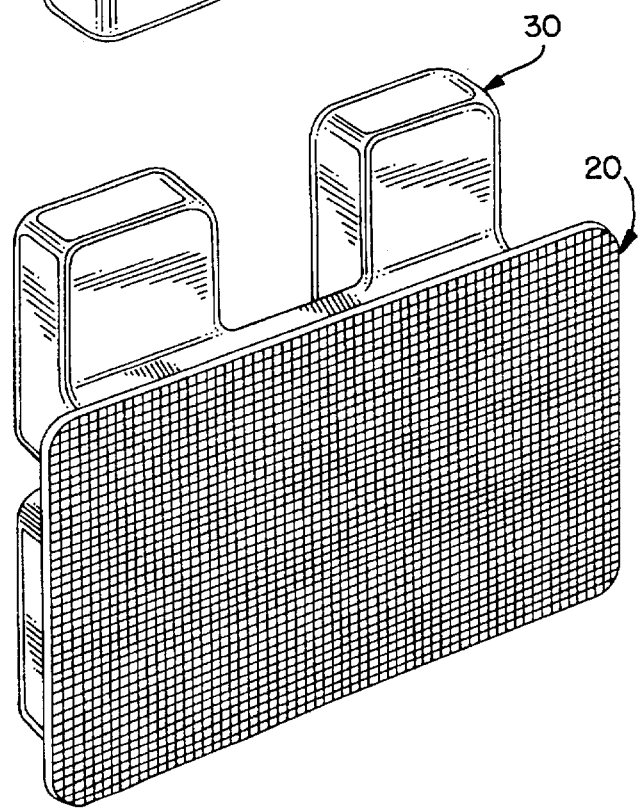
FIG. 6 is a perspective view of the backside of an orthodontic bracket showing the bonding pad of the present invention secured to the bracket.
Figure 7:
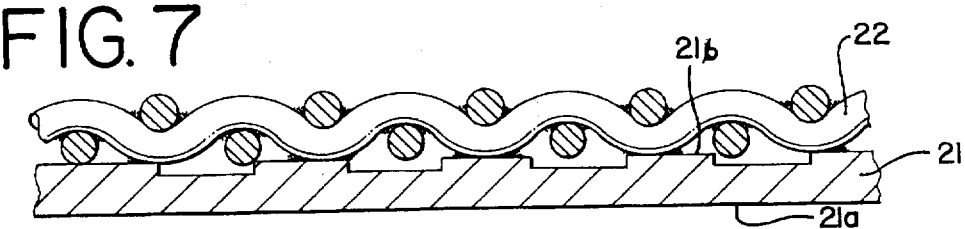
FIG. 7 is a greatly enlarged cross-sectional view taken through a bonding pad according to the present invention and illustrating the foil with a photoetched surface and a layer of mesh material suitably bonded to the foil such as by diffusion bonding.

FIG. 7 shows a cross section taken through the bonding pad of FIG. 3, wherein it is seen that the mesh layer 22 is secured to the photoetched foil 21. The foil 21 includes a substantially smooth surface 21a that would be suitably secured to the base of an orthodontic attachment, as illustrated in FIGS. 5 and 6, such as by brazing or soldering, thereby mounting the pad on an attachment. The other side of the foil includes a photoetched surface 21b which would serve as a secondary interlock with the bonding material once the bracket is applied to a tooth and secured thereto with a bonding material. The mesh layer 22 secured to the surface 21b provides a primary interlock with the bonding material. The composite bonding pad thereby greatly increases the bonding strength between a bracket and a tooth.

Following the lamination of the mesh to the photoetched surface of the foil, the surfaces of the photoetched side and the mesh may be treated to further enhance bonding, by additionally roughing the laminate to increase surface area as previously suggested with the foil 11a. A preferable method would involve sandblasting with $Al_2O_3$ grit in the range of 50 to 90 micron ($\mu$) sizes.

It will be appreciated that any suitable bonding material may be used with the bonding pad of the present invention, including those bonding materials marketed by American Orthodontics Corporation of Sheboygan, Wis., and particularly including their NO MIX:30 adhesive, their SPECTRUM light-cured adhesive, their FORCE II paste adhesive, and their Eagle No Drift highly filled, viscous, light-curable adhesive. NO MIX:30, SPECTRUM, FORCE II, and EAGLE NO DRIFT are trademarks owned by American Orthodontics Corporation.

As further seen in FIGS. 5 and 6, the bonding pad 20 of the invention is secured to an orthodontic bracket 30 by soldering, brazing, welding, or any other suitable means so that the bonding pad is securely connected to the base of the bracket, which is then adapted to be suitably bonded to a tooth in a patient's mouth. It should further be appreciated that the bonding pad of the present invention may be used on other orthodontic attachments for the mouth of a patient such as buccal tubes or lingual buttons.

The preferred bonding pad of the invention is shown in FIG. 10 and generally indicated as 40. It consists of 0.007 inch thick photoetched stainless steel foil 41 diffusion bonded to 80 mesh count stainless steel mesh 42 with 0.0045 inch diameter wires 43 and 44 extending at right angles to each other, thereby defining substantially square openings and forming a laminated assembly. The mesh is arranged 45° to the foil substrate. The photoetched foil includes substantially square pockets 45, 0.008×0.008 inches with a depth of 0.0017 inch ±0.005 inch, substantially arranged in columns and rows with flats or lands 46 of 0.004 inches between pockets. The laminate is then sandblasted with 50μ $Al_2O_3$ grit.

Orthodontic brackets made with the bonding pad of the above preferred embodiment provide significantly improved bond strengths compared to heretofore known bonding pads for metal brackets, including stock or standard foil/mesh brackets produced by American Orthodontics Corporation, the assignee of this application, and recently released brackets of competitors claiming exceptional bond strength.

Shear-bond tests were conducted on the four bracket models above identified. The facial surfaces of bovine teeth were ground flat, and the teeth were mounted in acrylic (methylmethacrylate powder/liquid). Maxillary central incisor brackets with pads were bonded to the teeth with Eagle No Drift adhesive/sealant according to manufacturers' recommendations. The areas of the bonding pads were measured using CAD software, wherein the pads of the standard and preferred models were 10.5625 $mm^2$, while the pads of the brackets having double mesh layers of 80 and 150 mesh like in above U.S. Pat. No. 4,889,485 (Co. X) were 12.5 $mm^2$, and pads of the brackets having flame-sprayed 100 mesh like in above U.S. Pat. Nos. 5,295,823 and 5,480,301 (Co. Y) were 10.0625 $mm^2$. The teeth were then fixtured in an Instron testing machine (Model 1123) and shear-bond tested utilizing a load setting of 20 kg and a crosshead speed of 0.5 mm/min. Twenty brackets of each model were included in each subsample. Table I below states the results of the average load at failure in kilograms (kg).

TABLE I

| Standard Foil/Mesh | Co. X | Co. Y | Preferred per Invention (Pad 40 of FIG. 10) |
| --- | --- | --- | --- |
| 6.99 | 7.95 | 7.04 | 7.66 |

Based upon bond pad area, the average megapascals (Mpa) values (newtons/$mm^2$) for the bonding pads tested are shown in Table II. One pascal is equivalent to one newton/square meter, and each kilogram of force is equivalent to 9.8 newtons.

TABLE II

| Standard Foil/Mesh | Co. X | Co. Y | Preferred per Invention |
| --- | --- | --- | --- |
| 6.49 | 6.23 | 6.86 | 7.11 |

This illustrates that the present invention exhibits a greater bonding strength than the bonding pads of the prior art.

Further the mode of interfacial failure between the bracket bonding pads and the teeth under the above tests was analyzed. This failure mode relates to the location of the failure when the brackets with the pad debond from the tooth surface under the shearing force. The types of failure that may be encountered include bracket/adhesive where the failure is at the bonding pad, enamel/adhesive where the failure is at the enamel of the tooth, and within/adhesive where the failure is detected within the adhesive and essentially between the enamel and the bracket pad. The preferred failure mode is the enamel/adhesive or within/adhesive mode because either indicates a stronger bracket pad/adhesive interface. These preferred failures not only indicate higher bond strength clinically but they also result in reduced clean-up time of adhesive remaining on the tooth following the termination of orthodontic treatment and removal of brackets. The following Table III sets forth the results of the tests of the brackets tested as to interfacial failure in percent of failure types for each subsample.

TABLE III

| | INTERFACIAL FAILURE (%) | | |
| --- | --- | --- | --- |
| | Enamel/ Adhesive | Within/Adhesive (cohesive) | Bracket/ Adhesive |
| Standard Foil/Mesh | 0 | 0 | 100 |
| Co X | 0 | 0 | 100 |
| Co Y | 5 | 5 | 90 |
| Preferred per Invention | 20 | 20 | 60 |

As above shown, the standard foil/mesh brackets exhibited failure 100 percent of the time at the bracket/adhesive face, or at the bonding pad which would thereby leave the maximum amount of adhesive on the tooth to be removed following removal of the bracket from the tooth. Similarly, the tests show that the brackets with bonding pads according to Company X (Co X) exhibit bracket/adhesive failure 100 percent of the time. The brackets with bonding pads according to Company Y (Co Y) exhibited failure at the bracket/adhesive face 90 percent of the time and 5 percent of the time at the enamel/adhesive face and 5 percent of the time at the within/adhesive face. Finally, the preferred form of the bracket of the present invention exhibited failure at the bracket/adhesive face only 60 percent of the time while exhibiting failure at the enamel/adhesive face 20 percent of the time and at the within/adhesive face 20 percent of the time. Accordingly, it can be appreciated the brackets with bonding pads according to the present invention exhibit substantially enhanced bond strength based upon pad square area and mode of interfacial failure than the brackets with bonding pads of the prior art.

In view of the foregoing, it may be appreciated that the bonding pad of the present invention provides an enhanced bonding arrangement between an orthodontic attachment and a tooth by providing a greater bonding strength that will maintain the integrity of the bond and the securing of the attachment on the tooth of a patient throughout the treatment of a patient and later reduces clean-up time after bracket removal.

It will be understood that modifications and variations may be effected without departing from the scope of the novel concepts of the present invention, but it is understood that this application is to be limited only by the scope of the appended claims.

The invention is hereby claimed as follows:

1. A metal bonding pad for an orthodontic attachment which comprises:
   a thin layer of metal foil having a substantially smooth side adapted to be secured to the backside of an orthodontic attachment and a bond side for coacting with a bonding material to bond to a tooth,
   said bond side having a photoetched pattern,
   and a layer of mesh diffusion bonded thereto.

2. The pad of claim 1, wherein said bond side includes means to increase the area contacting the bonding material.

3. The pad of claim 2, wherein said means includes a sandblast finish on the mesh layer and photoetched pattern.

4. The pad of claim 2, wherein said means for increasing the bond side area is selected from a group consisting of (a) sandblasting, (b) flame spraying, (c) ion bombardment, and (d) plasma etching.

5. The pad of claim 1, wherein the mesh layer is woven.

6. A metal bonding pad for an orthodontic attachment which comprises:

a layer of metal having a substantially smooth side adapted to be secured to the backside of an orthodontic attachment and a bond side for coacting with a bonding material to bond to a tooth, said bond side having a photoetched pattern, and a layer of mesh diffusion bonded thereto, wherein the photoetched pattern includes a plurality of generally square pockets arranged substantially equidistant from each other in rows and columns, and the mesh is of woven wire and includes generally a plurality of substantially equally sized square openings defined by one series of wires running at right angles to a second series of wires.

7. The pad of claim 6, wherein said pockets are about 0.008 inches×0.008 inches at a depth of about 0.0017 inches ±0.0005 inches and the flats between pockets are about 0.004 inches.

8. The pad of claim 7, wherein the mesh layer count is in the range of about 50 to 100, with a wire size of about 0.003 to 0.0075 inch.

9. The pad of claim 7, wherein the mesh layer count is 80, and the wire size is 0.0045 inch.

10. The pad of claim 8, wherein the mesh layer count is 80, with a wire size of about 0.0045 inch.

11. The pad of claim 10, wherein the wires of the mesh layer are oriented at 0° to the photoetched pattern.

12. The pad of claim 11, wherein the wires of the mesh layer are oriented at 45° to the photoetched pattern.

13. Metal bonding pad material for making bonding pads for orthodontic attachments to be bonded to teeth by a bonding material, said material comprising:

a thin layer of foil metal having one side that is substantially smooth for securing to the base of an attachment and the opposite side being photoetched to provide a secondary interlock with a bonding material, and a layer of mesh secured to the photoetched side of said foil to provide a primary interlock with the bonding material.

14. The material of claim 13, wherein the photoetched side of the foil is treated to further coact with the bonding material to enhance the bond strength of the material.

15. Metal bonding pad material for making bonding pads for orthodontic attachments to be bonded to teeth by a bonding material, said material comprising:

a layer of foil having one side that is substantially smooth for securing to the base of an attachment and the opposite side being photoetched to provide a secondary interlock with a bonding material, and a layer of mesh secured to the photoetched side of said foil to provide a primary interlock with the bonding material, wherein the photoetched side includes a plurality of generally square pockets arranged substantially equidistant from each other in rows and columns, and the mesh is of woven wire and includes generally a plurality of substantially equally sized square openings defined by one series of wires running at right angles to a second series of wires.

16. The material of claim 15, wherein the photoetched side includes a substantially symmetrically arranged pattern of substantially square pockets.

17. The material of claim 16, wherein the wires of the mesh layer are oriented at 0° to the pattern of pockets.

18. The material of claim 16, wherein the wires of the mesh layer are oriented at 45° to the pattern of pockets to provide the maximum coaction of the wires to the pockets.

19. A method of improving the bonding characteristics of an orthodontic appliance having a metallic bonding pad with a tooth contact surface, wherein the bonding pad includes a thin layer of metal foil and a layer of woven metal mesh with wires arranged perpendicularly to each other, said method comprising the steps of:

photoetching a pattern of substantially square pockets onto one side of said metal layer, and diffusion bonding the layer of mesh to the photoetched side of the metal layer.

20. The method of claim 19, which further includes the step of treating the surfaces of the photoetched pattern and the mesh wires to enhance their bondability to bonding material.

21. The method of claim 20, which includes the further step of orienting the wires of the mesh layer at 45° to the photoetched pattern.

22. The method of claim 20, wherein the step of treating the surfaces of the pattern and the mesh wires includes sandblasting with aluminum oxide grit.

23. The method of claim 22, wherein the grit size is 50 to 100 micron.

24. The method of claim 22, wherein the grit size is 50 micron.

25. A method of improving the bonding characteristics of an orthodontic appliance having a metallic bonding pad with a tooth contact surface, wherein the bonding pad includes a layer of metal foil and a layer of woven metal mesh with wires arranged perpendicularly to each other, said method comprising the steps of:

photoetching a pattern of substantially square pockets onto one side of said metal layer, diffusion bonding the layer of mesh to the photoetched side of the metal layer, treating the surfaces of the photoetched pattern and the mesh wires to enhance their bondability to bonding material, and orienting the wires of the mesh layer at 0° to the photoetched pattern.

26. An orthodontic bonding pad in the form of a laminate for enhancing the bonding strength of an appliance bonded to a tooth by a suitable bonding material which comprises:

a first layer of thin metal foil having a smooth side attachable to the appliance and a textured side in the form of a photoetched pattern of recesses, and a second layer of metal mesh of woven wire strands diffusion bonded to the textured side of the metal foil.

27. The bonding pad of claim 26, which further includes means for further enhancing the bonding strength.

28. The bonding pad of claim 27, wherein said means comprises sandblasting the surfaces of the textured side and the mesh.

29. The bonding pad of claim 27, wherein said means comprises sandblasting the surfaces of the textured side and the mesh with aluminum oxide grit.

30. The bonding pad of claim 27, wherein said means comprises sandblasting the surfaces of the textured side and the mesh 50 to 100 micron aluminum oxide grit.

\* \* \* \* \*